United States Patent
Behler et al.

(10) Patent No.: US 8,546,446 B2
(45) Date of Patent: Oct. 1, 2013

(54) ANIONIC ISOSORBIDE DERIVATIVES AND THEIR USE

(75) Inventors: Ansgar Behler, Bottrop (DE); Catherine Breffa, Düsseldorf (DE); Hans-Christian Raths, Monheim (DE); Thorsten Löhl, Schmallenberg (DE)

(73) Assignee: Cognis IP Management GmbH, Duesseldorf (DE)

( * ) Notice: Subject to any disclaimer, the term of this patent is extended or adjusted under 35 U.S.C. 154(b) by 440 days.

(21) Appl. No.: 12/818,346

(22) Filed: Jun. 18, 2010

(65) Prior Publication Data

US 2010/0324153 A1 Dec. 23, 2010

(30) Foreign Application Priority Data

Jun. 18, 2009 (EP) .................. 09007986

(51) Int. Cl.
*A61K 31/34* (2006.01)

(52) U.S. Cl.
USPC ............................ 514/461; 514/468; 514/469

(58) Field of Classification Search
USPC ........................... 514/461, 468, 469
See application file for complete search history.

(56) References Cited

U.S. PATENT DOCUMENTS

| 4,150,151 | A | * | 4/1979 | Pader et al. ................. 424/56 |
| 5,153,000 | A | * | 10/1992 | Chikawa et al. ............. 424/450 |
| 7,544,648 | B2 | * | 6/2009 | Sakai et al. ................. 510/126 |
| 2002/0174596 | A1 | | 11/2002 | Deflort et al. |

FOREIGN PATENT DOCUMENTS

| EP | 1106616 | 6/2001 |
| WO | 01/01949 | 1/2001 |

OTHER PUBLICATIONS

Molinier et al, "Isosorbide: A sustainable diol derived from sorbitol for the synthesis of new amphiphiles,"CORM V Conference, Jan. 20, 2009, XP002542239 Lisbon, Portugal.
Molinier et al., "Isosorbide: a versatile polar block derived from sorbitol for the design of novel amphiphilic species, ranging from solvents to surfactants," CESIO 7th World Surfactants Congress, Paris, Jun. 22, 2008-Jun. 25, 2008, 8 pages.
Saheki et al., "Synthesis of 2-Alkyloyl-1,4,3,6-Dianhydrosorbitol-5-Sulfates and Evaluation of the Surface Active Properties,"JAOCS. vol. 63, No. 7 (Jul. 1986), pp. 927-930.
Zhu et al, "Isosorbide as a novel polar head derived from renewable resources. Application to the design of short-chain amphiphiles with hydrotropic properties," Green Chem., 2008, 10, pp. 532-540.

* cited by examiner

*Primary Examiner* — Sreeni Padmanabhan
*Assistant Examiner* — Shobha Kantamneni
(74) *Attorney, Agent, or Firm* — Servilla Whitney LLC

(57) ABSTRACT

Disclosed are isosorbide derivatives according to the following general formula

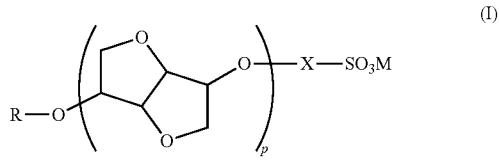

(I)

wherein R represent a hydrogen atom, or an alkyl group with 6 to 22 C-atoms, or an acyl group, or a group $X-SO_3M$, and M stands for a cation, a hydrogen atom or an alkali metal atom or an ammonium or an alkylammonium ion, and X represents an alkoxylated derivative $(AO)_n$, wherein AO represents a group $C_2H_4O$, or $C_3H_6O$, or any mixtures thereof, and the index n is zero or 1 to 20, and p represents a number between 1 and 10, preferably between 1 and 4, and the use thereof to prepare cleansers, detergents, personal care compositions, or cosmetic compositions.

6 Claims, 1 Drawing Sheet

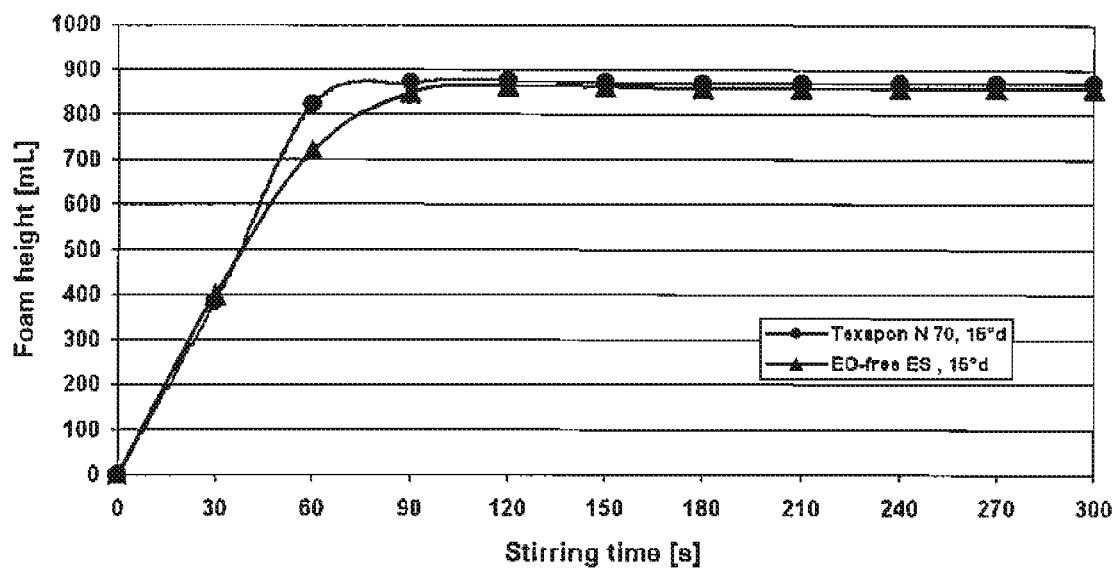

ANIONIC ISOSORBIDE DERIVATIVES AND THEIR USE

BACKGROUND OF THE INVENTION

The present application pertains to specific anionic derivatives of isosorbide, and the use thereof in household products, like detergents or in cosmetic applications, preferably in personal cleaning applications, detergents and manual dish detergents.

The most widely used anionic surfactants in cleansing compositions are alkyl sulphates, to polyoxyethylene alkyl sulphates and alkyl benzene sulphonates. These compounds are known to have a good foaming and deterging power. Due to their harshness, however, they are not desirable as components for cleansing compositions topically applied to human skin and hair. Their damaging effect particularly where young, tender or damaged skin is involved, has been the subject of intense study for many years.

On the other hand milder surfactants often suffer from the drawback that they do not provide high foam which is very important for the consumer. Therefore, there is a strong need for products which are not only very mild but also possess an excellent foaming power.

Isosorbide (or 1,4:3,6-dianhydrosorbitol, see formula below) is the anhydride of sorbitol:

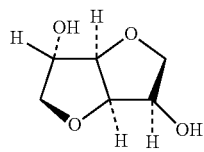

Upon heating sorbitol for example with concentrated sulfuric or hydrochloric acid, two molecules of water are eliminated with the formation of isosorbide. So far, these compounds are also known generally as dianhydrohexitols (including besides isosorbide also the isomers isomannide and isoidide).

Certain derivatives of isosorbide are known, especially esters or ethers thereof. Furthermore it is known to use isosorbide derivatives as additives in various applications, like detergents, cleansers or cosmetic compositions. US 2002/0174596 A1 discloses various isosorbide ethers as detergent for fuels. WO 01/0191949 A1 describes dimethyl-isosorbide as compound of a personal cleansing composition.

It is an object of the present invention to find new additives, useful in detergents and cleansers, and based on isosorbide chemistry. It was found that certain anionic derivatives of isosorbide could be used with advantage in detergent, cleansers and related products, but preferably in personal cleaning applications.

SUMMARY OF THE INVENTION

The present application pertains in a first embodiment to isosorbide derivatives according to general formula (I)

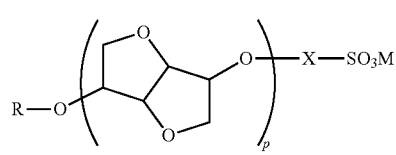

wherein R represents a hydrogen atom, or an saturated or unsaturated, branched or linear alkyl group with 6 to 22 C-atoms, or an acyl group, or a group $X$—$SO_3M$, and M stands for a cation, a hydrogen atom or an alkali metal atom or an ammonium or an alkylammonium ion, and X represents an alkoxylated derivative $(AO)_n$ wherein AO represents a group $C_2H_4O$, $C_3H_6O$ or $C_4H_8O$, or any mixtures thereof, and the index n is zero or 1 to 20, and p represents a number between 1 and 10, preferably between 1 and 4, with the exception of a derivative according to formula (I) wherein R represents a dodecyl moiety, X is a group $(C_2H_4O)_3$, and p is 1.

The derivatives according to formula (I) encompasses mono- and disulphonated compounds, as well as blends thereof. Compounds according to formula (I) can be prepared by reacting isosorbide, or an isosorbide monoalkylether with know sulphonation agents, preferably with chlorosulphonic acid (Cl—$SO_3H$) or $SO_3$/Pyridine complex in an aprotic solvent, like tetrahydrofuran.

A preparation example for one specific isosorbide ether sulphate is given in the poster by V. Molinier et al., Title: "Isosorbide: a versatile polar block derived from sorbitol for the design of novel amphiphilic species, ranging from solvents to surfactants", presented on the CESIO $7^{th}$ World Surfactant Congress, held in Paris from 22 Jun. till 25 Jun. 2008. As this document discloses one single ethoxylated isosorbide ether sulfate on page 3 (named SDIsoS) this single compound is disclaimed from the coverage of this application.

DESCRIPTION OF THE PREFERRED EMBODIMENTS

Preferred compounds according to formula (I) contain as moiety R a hydrogen atom (thus, these preferred compounds are mono ethers) whereby X represents an alkoxylated moiety $(AO)_n$ as defined above. Preferred groups X are $(CH_2CHR'$—$O)_n$, whereby n is a number between 0 and 20, preferably 2 to 8, and R' represents H, or an group —$C_3$ or a group —$CH_2$—$CH_3$. Also mixed alkoxylates, containing for example ethylenoxide and propylenoxide groups together (here are random as well as block distribution of the different alkoxides are possible) are falling within the definition of formula (I). M is a cation, and preferably an alkali metal atom and here in particular sodium. Because of the method of synthesis, there are side products possible, for instance, sulfonated isosorbide diethoxylates, up to an amount of at maximum 10% by weight, preferably up to 5% by weight or even less. The R group in formula (I) could be hydrogen, an alkyl moiety as defined, or an acyl group R—CO (in this case the derivative contains an ester group), wherein R also as preferred matter represents an alkyl group with 2 to 22 C-atoms, preferably 4 to 18 C-atoms.

In general R could represent saturated as well as mono, or poly unsaturated alkyl or alkenyl groups. It will also but independently stand for branched or linear moieties. The teaching of the present application encompasses also the use of any mixtures of any different isosorbide derivatives too.

The formula (I) also encompasses oligomeric isosorbide, as far as the index p in formula (I) represents a figure of 2 to 4. Those oligomers could be obtained by acid catalyzed oligomerisation of isosorbides.

A further preferred compound according to formula (I) is free of any alkoxylated moiety, i.e. the index n is zero.

The isosorbide derivatives according to this application show a positive effect on foam height, foam volume, and/or foam tactile properties in aqueous systems.

Therefore, a further embodiment of the invention pertains to the use of compounds according to formula (II)

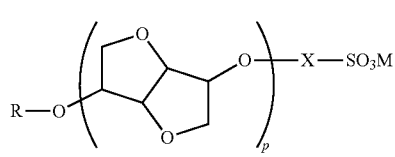

(II)

wherein R represent a hydrogen atom, or a saturated or unsaturated, linear or branched alkyl group with 6 to 22 C-atoms, or a saturated or unsaturated, linear or branched acyl group, or a group X—SO$_3$M, and M stands for a cation, a hydrogen atom or an alkali metal atom or an ammonium or an alkylammonium ion, and X represents an alkoxylated derivative (AO)$_n$ wherein AO represents a group $C_2H_4O$, or $C_3H_6O$, or any mixtures thereof, and the index n is zero or 1 to 20, and p represents a number between 1 and 10, preferably between 1 and 4, to prepare cleansers, detergents, personal care compositions, or cosmetic compositions. The R group in formula (II) could be hydrogen, an alkyl moiety as defined, or an acyl group R—CO (in this case the derivative contains an ester group), wherein R also as preferred matter represents an alkyl group with 2 to 22 C-atoms, preferably 4 to 18 C-atoms.

So far compounds following formulas (I) or (II) are useful for the preparation of all kind of detergents, cleansers and the like (solid, liquid or gel-like ones) or the use of this compounds in cosmetic compositions. Preferred is the use of compounds according to formula (II) in cleaners and here in particular for cleaners for hard surfaces, like kitchen or bathroom cleaner or dish washing detergents (manual and automatic). Formula (II) is identical to formula (I) but will not exclude the single compound as in formula (I).

The isosorbide derivatives according to formula (II) then may be present in amounts from 0.1 up to 25% by weight, dependent on the particular formulation. Preferably those detergents or cleansers will contain the isosorbide derivatives in amounts of 1 to 15 wt %, and most preferred from 5 to 10 wt %, based on the total weight of the cleanser or detergent.

The isosorbide derivatives according to formula (II) are particularly useful in home care applications, like detergents, and all kind of cleaners (kitchen, bathroom, hard surface, automotive or car cleansers, and multipurpose cleansers), as well as in dishwashing compositions (hand and automatic dish washing) and in personal care compositions, especially in hair and body cleansing formulations, but can also used with advantage in cosmetic compositions, for example in shampoos, creams and the like.

Preferred is the use of the isosorbide derivatives inter alia in personal care compositions such as a liquid soap, shampoo, foam bath, shower bath and the like or a solid form such as a bar which can illustratively be a soap or syndet composition. The isosorbide derivatives could also be used in toothpaste and related compositions, like mouth wash. In addition to surfactants or surfactant combinations, the cosmetic products in question typically contain such constituents as emulsifiers, oil components, solubilizers, thickeners, superfatting agents, biogenic agents, film formers, fragrances, dyes, pearlescers, foam stabilizers, preservatives and pH regulators. Accordingly, the preparations according to the invention may contain additional components and auxiliaries as known from the prior art.

Any detergent or cleanser compositions according to the invention may contain, besides the isosorbide derivatives other surfactants, builders, salts, bleaching agents, bleach activators, optical brighteners, redeposition inhibitors, soil repellants, solubilizers, foam inhibitors, perfumes, buffers, non-aqueous solvents, dyes and enzymes as auxiliaries and additives.

The cleaners according to the invention may further contain, for example, solubilizers, such as ethanol, isopropyl alcohol, ethylene glycol, diethylene glycol or preferably butyl diglycol, foam regulators, for example soap, soluble builders, for example citric acid or sodium citrate, EDTA or NTA, and abrasives as auxiliaries. In many cases, an additional bactericidal effect is required so that the multipurpose cleaners may contain cationic surfactants or biocides, for example glucoprotamine. The cleaners according to the invention may be both alkaline (pH>7.5) and acidic (pH<6.5). The isosorbide derivatives may be formulated with other surfactants, like anionic, nonionic, amphoteric and/or cationic surfactants.

Anionic surfactants according to the present invention include aliphatic sulfates, such as fatty alcohol sulfates, fatty alcohol ether sulfates, fatty acid polyglycol ester sulfates, dialkyl ether sulfates, monoglyceride sulfates and aliphatic sulfonates, such as alkane sulfonates, olefin sulfonates, ether sulfonates, n-alkyl ether sulfonates, ester sulfonates, and lignin sulfonates. Fatty acid cyanamides, sulfosuccinic acid esters, fatty acid isethionates, acylaminoalkane sulfonates (fatty acid taurides), fatty acid sarcosinates, ether carboxylic acids and alkyl (ether) phosphates may also be used for the purposes of the invention, but are not preferred. Preferred anionic surfactants in the sense of the present invention are selected from the group of fatty alcohol sulfates, fatty alcohol ether sulfates and/or fatty acid polyglycol ester sulfates, and mixtures thereof.

Typical examples of nonionic surfactants are alkoxylates of alkanols, end-capped alkoxylates of alkanols with no free OH groups, alkoxylated fatty acid lower alkyl esters, amine oxides, alkylphenol polyglycol ethers, fatty acid polyglycol esters, fatty acid amide polyglycol ethers, fatty amine polyglycol ethers, alkoxylated triglycerides, mixed ethers and mixed formals, fatty acid-N-alkyl glucamides, protein hydrolyzates (more particularly wheat-based vegetable products), polyol fatty acid esters, sugar esters, sorbitan esters and polysorbates. If the nonionic surfactants contain polyglycol ether chains, they may have a conventional homolog distribution although they preferably have a narrow homolog distribution. The other nonionic surfactants are preferably selected from the group consisting of alkoxylates of alkanols, more particularly fatty alcohol polyethylene glycol/polypropylene glycol ethers or fatty alcohol polypropylene glycol/polyethylene glycol ethers, end-capped alkoxylates of alkanols, more particularly end-capped fatty alcohol polyethylene glycol/polypropylene glycol ethers or end-capped to fatty alcohol polypropylene glycol/polyethylene glycol ethers, and fatty acid lower alkyl esters and amine oxides.

Alkyl and alkenyl oligoglycosides are known, and preferred, nonionic surfactants which correspond to formula R—O-[G]$_p$ in which R is an alkyl and/or alkenyl group containing 6 to 22 carbon atoms, G is a sugar unit containing 5 or 6 carbon atoms and p is a number of is 1 to 10. They may be obtained by the relevant methods of preparative organic chemistry. The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p in general formula (V) indicates the degree of oligomerization (DP), i.e. the distribution of mono- and oligoglycosides, and is a number of 1 to 10.

Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the application point of view. The alkyl or alkenyl group R may be derived from primary alcohols containing 4 to 11 and preferably 8 to 10 carbon atoms.

Typical examples of cationic surfactants are quaternary ammonium compounds and quaternized fatty acid trialkanolamine esters. Typical examples of amphoteric or zwitterionic surfactants are alkyl betaines, alkyl amidobetaines, aminopropionates, aminoglycinates, imidazolinium betaines and sulfobetaines.

A further preferred embodiment of the present invention pertains to the use of the isosorbide derivatives according to formula (II) in the presence of electrolyte salts as thickening agent for aqueous systems, and especially for those surfactant mixes, which are difficult to thicken. In this regard "thickening" simply means any increase of viscosity of the aqueous compositions. The isosorbide derivatives will act in combination with an electrolyte salt, like sodium potassium or magnesium salts, ammonium salts or anorganic sulfates. Suitable inorganic electrolyte salts are any water-soluble alkali metal, ammonium and alkaline earth metal salts, for example the fluorides, chlorides, bromides, sulfates, phosphates and nitrates and hydrogen carbonates, providing they are soluble in water in a quantity of at least 1% by weight at 20° C. The chlorides or sulfates of an alkali metal, ammonium or magnesium are preferably used, sodium chloride and magnesium chloride being particularly preferred.

Thickening of aqueous systems containing alkyl ether sulfates with such electrolytes is commonly used in industry. However, as far as surfactants free of any alkoxy groups are concerned this simple and cost efficient thickening concept will not function well.

It is therefore one of the aims of this invention to provide surfactants free of ethoxylated (or propoxylated) moieties, which can nevertheless be thickened by electrolyte salts, in particular sodium chloride. Consequently, the use of such compounds according to formula (II) is preferred wherein no group AO is present (i.e. the index n is zero).

The amount of electrolyte depends on the kind and amount of surfactants in the particular compositions and can be easily determined by the skilled in the art. However, typical amounts of salts are in the range from 0.1 to 10, preferably 0.5 to 4 weight-%, based on the total weight of the aqueous composition. In this regard the amount of isosorbide derivatives could be preferably adjusted in a range from 1 to 15 weight-%, based on the total weight of the aqueous formulation.

EXAMPLES

Preparation of an Isosorbide Ether Sulfate

Example 1

A solution of 1 mol isosorbide (146 g) in 400 ml tetrahydrofuran (THF) was prepared at 15° C. At this temperature 2.1 mol Cl—SO$_3$H (244.7 g) were added slowly, not exceeding 25° C., while purging the whole reaction unit with nitrogen to remove the generated HCl. After completing the reaction the mixture is added to a 50 wt % solution of NaOH in water, keeping the pH-value above 7. The THF water blend was removed by distillation and the residue was extracted and recrystallized with ethanol, giving 280 g of a white solid.

Example 2

A solution of 0.4 mol isosorbide mono dodecylether (134 g) in 400 ml THF was prepared at 15° C. At this temperature 0.42 mol Cl—SO$_3$H (48.9 g) was added slowly, not exceeding 25° C., while purging the whole reaction unit with nitrogen to remove the generated HCl. After completing the reaction the mixture is added to a 50 wt % solution of NaOH in water, keeping the pH-value above 7. The THF/water blend was removed by distillation and the residue was washed with hexane and dried, to yield 98 g of a white solid.

Performance Tests of the Isosorbide Sulfates

The isosorbide derivative according to example 2 (="EO-free ES") was tested in comparison to a C12/C14 fatty alcohol 2 EO ether sulfate (Texapon® N70; a product of Cognis) with regard to the foaming properties in a rotor foam test with 0.5 g/l active at 40° C. at pH=6. The method involves stirring an aqueous sample containing surfactant within a specified time. In addition or after the mechanical action, the volume of the resulting foam is mixed. The stirrer for stirring the sample rotates at a specified rpm. The stirrer rotates with a revolution rate of 900-1300 revolutions per minute. The total stirring time is 60-180 s. The actual level of foam is determined at specified times during the stirring operation. The tested isosorbide sulfate shows similar foam properties compared to Texapon® N70. In FIG. 1 the foam height is shown against the stirring time.

Thickening Test:

To show the thickening properties of the anionic isosorbide derivatives viscosity measurements have been conducted. The viscosity of an aqueous ether sulfate surfactant solution (Texapon® NSC—Cognis) and an alkylglucoside (Plantacare® 1200—Cognis) solution were tested, with and without electrolyte addition. As isosorbide derivative the component of example 2 where added. Plantacare contains MgCl and so far no addition of electrolyte was necessary.

All the components were mixed together and then the pH was set to 6 with citric acid. After all the bubbles were removed from the solution, the viscosity was measured with a Brookfield LVT Viscosimeter. (Spindle 4 @ 60 rpm, 20° C.). Data is shown in table 1 for the Texapon® and in table 2 for the Plantacare® product.

TABLE 1

| | | Viscosity (mPas) Addition of wt % NaCl | | |
|---|---|---|---|---|
| | Amount | 2 | 3 | 4 |
| Texapon NSO | 12% | 19 | 590 | 12.800 |
| Texapon NSO Additive | 12% 2% | 220 | 13.000 | 70.000 |

TABLE 2

| | Amount | Viscosity (mPas) | |
|---|---|---|---|
| Plantacare 1200 | 12% | 1.425 | |
| Plantacare 1200 Additive | 12% 2% | | 5.400 |

These results show that the isosorbide derivatives are able to thicken aqueous compositions.

The invention claimed is:

1. A cleanser, detergent, personal care or cosmetic composition, said composition comprising: an isosorbide derivative according to general formula (II)

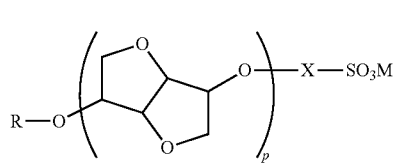

(II)

wherein R represent a hydrogen atom, or a saturated or unsaturated, branched or linear alkyl group with 6 to 22 C-atoms, or a group X—$SO_3M$, and M stands for a cation, a hydrogen atom or an alkali metal atom or an ammonium or an alkylammonium ion, and X represents an alkoxylated derivative $(AO)_n$ wherein AO represents a group $C_2H_4O$, or $C_3H_6O$, or any mixtures thereof, and the index n is 1 to 20, and p represents a number between 1 and 10, with the exception of a derivative according to formula (II) wherein R represents a dodecyl moiety, X is an group $(C_2H_4O)_3$, and p is 1; and an electrolyte selected from the group consisting of water-soluble alkali metal, ammonium and alkaline earth metal salts of fluorides, chlorides, bromides, sulfates, phosphates and nitrates and hydrogen carbonates, wherein the isosorbide derivative of formula (II) in the presence of said electrolyte is a thickening agent for aqueous systems.

2. The composition according to claim 1, wherein the isosorbide derivative is present in amounts from 0.1 to 25 wt %, based on the total weight of the cleanser, detergent, personal care or cosmetic composition.

3. The composition according to claim 1 wherein the isosorbide derivative of formula (II) in the presence of said electrolyte is a thickening agent for alkyl or alkenyl oligoglycoside-based aqueous formulations.

4. A method of preparing a cleanser, detergent, personal care or cosmetic composition, said method comprising combining at least one component of a cleanser, detergent, personal care or cosmetic composition with at least one isosorbide derivative according to general formula (II)

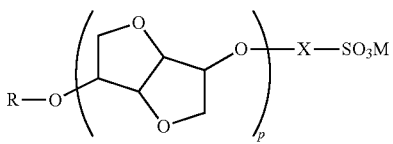

(II)

wherein R represent a hydrogen atom, or a saturated or unsaturated, branched or linear alkyl group with 6 to 22 C-atoms, or a group X—$SO_3M$, and M stands for a cation, a hydrogen atom or an alkali metal atom or an ammonium or an alkylammonium ion, and X represents an alkoxylated derivative $(AO)_n$ wherein AO represents a group $C_2H_4O$, or $C_3H_6O$, or any mixtures thereof, and the index n is 1 to 20, and p represents a number between 1 and 10, with the exception of a derivative according to formula (II) wherein R represents a dodecyl moiety, X is an group $(C_2H_4O)_3$, and p is 1; and combining said at least one isosorbide derivative according to general formula (II) with an electrolyte selected from the group consisting of water-soluble alkali metal, ammonium and alkaline earth metal salts of fluorides, chlorides, bromides, sulfates, phosphates and nitrates and hydrogen carbonates to provide thickening for aqueous systems.

5. The method according to claim 4, wherein the isosorbide derivative is present in amounts from 0.1 to 25 wt %, based on the total weight of the cleanser, detergent, personal care or cosmetic composition.

6. The method of claim 4, wherein said aqueous system is an alkyl or alkenyl oligoglycoside-based aqueous formulation.

* * * * *